United States Patent [19]

Nomura et al.

[11] Patent Number: 5,534,229
[45] Date of Patent: Jul. 9, 1996

[54] VOLATILIZATION SUPPRESSING AGENT

[75] Inventors: Ryuji Nomura; Haruo Shibatani, both of Tokyo, Japan

[73] Assignee: Nomura & Shibatani, Tokyo, Japan

[21] Appl. No.: 360,131

[22] Filed: Dec. 20, 1994

Related U.S. Application Data

[63] Continuation of Ser. No. 120,912, Sep. 15, 1993, abandoned.

[30] Foreign Application Priority Data

Sep. 16, 1992 [JP] Japan ................................ 4-270767

[51] Int. Cl.$^6$ ........................... A61L 9/01; A61L 9/04; A61L 9/12
[52] U.S. Cl. ..................... 422/123; 422/5; 422/305; 424/76.4; 239/44; 239/60
[58] Field of Search ............................. 422/5, 305, 120, 422/123; 424/76.2, 76.4; 239/44, 60

[56] References Cited

U.S. PATENT DOCUMENTS

| | | | |
|---|---|---|---|
| 3,954,964 | 5/1976 | Kuderna, Jr. .................... | 424/76.2 X |
| 4,128,507 | 12/1978 | Mitzner ............................ | 424/76.4 X |
| 4,286,754 | 9/1981 | Jones ................................ | 239/44 X |
| 4,413,779 | 11/1983 | Santini ............................. | 239/44 X |
| 4,719,040 | 1/1988 | Traas et al. ...................... | 512/4 |
| 4,809,912 | 3/1989 | Santini ............................. | 239/60 |
| 4,906,488 | 3/1990 | Pera ................................. | 426/573 |
| 4,913,350 | 4/1990 | Purzycki .......................... | 239/44 |

FOREIGN PATENT DOCUMENTS

| | | |
|---|---|---|
| 63-27361 | 11/1988 | Japan . |
| 1-34435A | 2/1989 | Japan . |
| 1-305043A | 12/1989 | Japan . |
| 3-124789 | 5/1991 | Japan . |
| 4-7385 | 1/1992 | Japan . |
| 4-231058A | 8/1992 | Japan . |
| 5-115539 | 5/1993 | Japan . |

*Primary Examiner*—Robert J. Warden
*Assistant Examiner*—E. Leigh Dawson
*Attorney, Agent, or Firm*—Wigman, Cohen, Leitner & Myers

[57] ABSTRACT

A volatilization suppressing agent comprising at least one thermosensitive polymer as an effective component is disclosed. Also disclosed is a volatile composition comprising a volatile effective component or an effective component carried by a volatile solvent and at least one thermosensitive polymer are disclosed. The use of the volatilization suppressing agent can suppress volatilization of volatile components when temperature rises and, as a result, volatilization of the volatile components is less affected by the temperature change. It is therefore possible to volatilize volatile components from air fresheners, deodorants, insecticides, moth proofers, repellents, attractants, antimicrobial agents, antifungal agents, antioxidants, and ozone decomposition agents more economically and to prevent troubles due to excessive volatilization.

12 Claims, 3 Drawing Sheets

VOLATILIZATION SUPPRESSING AGENT

This is a continuation of application Ser. No. 08/120,912 filed on Sep. 15, 1993 now abandoned.

BACKGROUND OF THE INVENTION

1. Field of the Invention

The present invention relates to a volatilization suppressing agent, and, more particularly, to a volatilization suppressing agent having a characteristic of aggregating or gelling above a certain temperature and useful for controlling the rate of volatilization of volatile compositions and the like, and to the use of such a volatilization suppressing agent.

2. Description of the Background Art

Volatile compositions, such as air fresheners, volatile moth proofers and repellents, volatile fungicidal agents, and the like, are conventionally known in the art. Such a volatile compositions may be a composition in which a volatile effective component is dissolved or solubilized in an aqueous solvent such as water, or a composition in which an effective component is carried by a volatile solvent.

In recent years, various methods have been proposed for volatilizing these volatile effective components or effective components carried by a volatile solvent at a constant rate (such volatile effective components or effective components carried by a volatile solvent are hereinafter collectively referred to as "volatile components").

The rate of volatilization of volatile components from these compositions, however, depends on that of the volatile effective components themselves or of the volatile solvent acting as a carrier. For this reason, there has been a problem, for example, that the rate of volatilization unduly increases under high temperature conditions, exhausting the effective components within a very short period of time and volatilizing them in an amount far exceeding the amount required for a specified space.

Conventionally, countermeasures for the problem relating to the fluctuations in the rate of volatilization due to temperature changes have consisted of changing the area from which the volatile components volatilize, or controlling the amount of air flow by manual, mechanical, or electrical means.

However, changing the volatilization area or manually controlling the amount of air flow according to the temperature change is extremely troublesome. In addition, since each person has an individual feeling toward temperature, it has been difficult to achieve the objects by these means.

Although the method of mechanically or electrically controlling the amount of air flow is free from such problems, this method has a drawback in that the devices for achieving the object are complicated and considerably expensive.

Development of a simple and inexpensive means for controlling the rate of volatilization has, therefore, been desired.

The present inventors have undertaken extensive studies concerning the method of suppressing the rate of volatilization of volatile components from volatile compositions at high temperatures, and found that the above objects can be achieved by suitably designing formulations of the volatile compositions, specifically by adding a compound which is hydrophilic at low temperatures, but aggregates or gels at high temperatures by losing its hydrophilic properties.

SUMMARY OF THE INVENTION

Accordingly, an object of the present invention is to provide a volatilization suppressing agent comprising at least one thermosensitive polymer as an effective component.

Another object of the present invention is to provide a volatile composition in which said volatilization suppressing agent is incorporated.

Still another object of the present invention is to provide a liquid air freshener system in which said volatilization suppressing agent is used.

As an preferred embodiment, the present invention provides a liquid air freshener system, comprising a container, a wick inserted into the container, and, optionally, a volatilizing plate at the top of said wick, said container containing a liquid air freshener or aromatic composition comprising at least one thermosensitive polymer.

Other and further objects, features and advantages of the present invention will be more fully evident from the following description.

DETAILED DESCRIPTION OF THE INVENTION AND PREFERRED EMBODIMENTS

Figure 1:
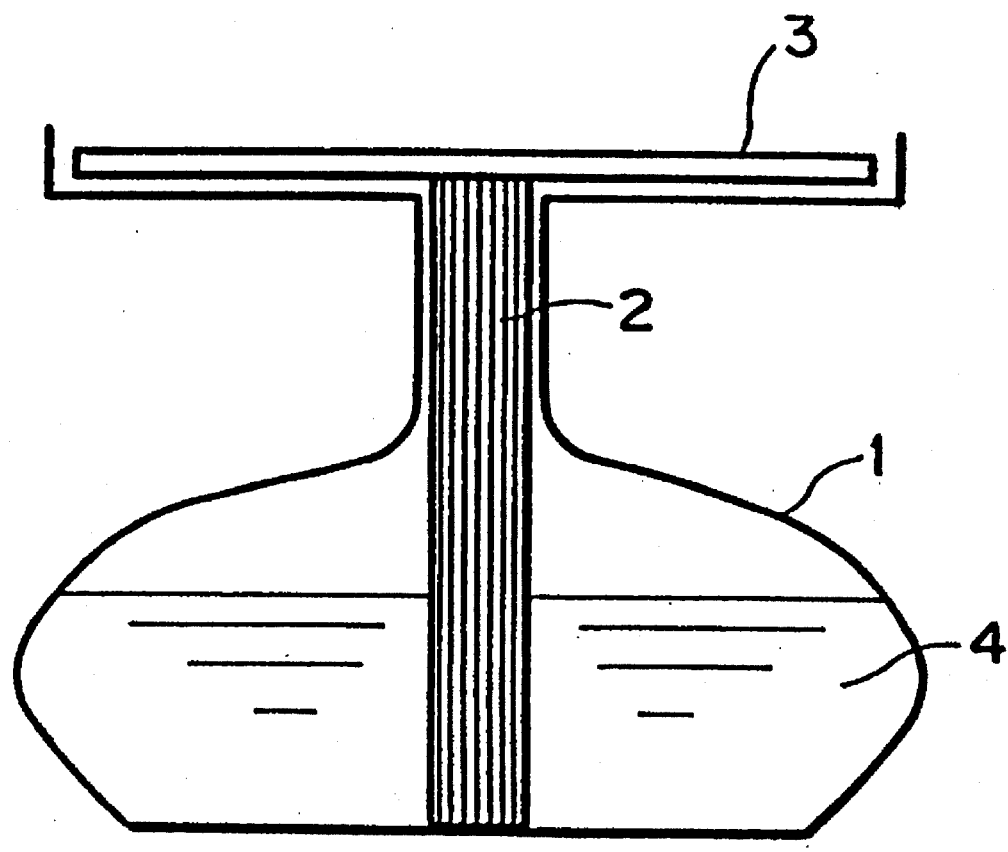
FIG. 1 shows an example of the structure of a liquid air freshener system of the present invention.

The thermosensitive polymer, the effective component of the volatilization suppressing agent of the present invention, is a polymer which has the characteristic of thermoreversibly aggregating or gelling when heated while dissolved in water. This polymer is hydrophilic at low temperatures but becomes hydrophobic at high temperatures by losing its hydrophilic properties.

Given as examples of the thermosensitive polymers are polyvinyl ethers such as polyvinyl methyl ether and poly-2-(2-methoxyethoxy)ethyl vinyl ether; polyvinyl alcohol derivatives such as partially acetylated polyvinyl alcohol; cellulose derivatives such as methylcellulose, hydroxypropylcellulose, and hydroxypropylmethylcellulose; polyalkylene oxides such as polyethylene oxide and polyethylene oxide-polypropylene oxide copolymers; polyacrylamide or polymethacrylamide derivatives such as poly-N-isopropylacrylamide, poly-N-isopropylmethacrylamide, and poly-N-methyl-N-ethylacrylamide; modified polyamides such as water-soluble nylon; and the like.

All these thermosensitive polymers are known polymers and readily available. For example, polyvinyl methyl ether can be manufactured by the cationic polymerization of methyl vinyl ether using a cation-type polymerization catalyst (e.g., boron fluoride, aluminum chloride), while cellulose derivatives such as methylcellulose can be manufactured by treating natural cellulose (pulp) with sodium hydroxide and reacting the treated product with an etherification agent (e.g., methyl chloride, propylene oxide, ethylene oxide).

Given as examples of commercially available thermosensitive polymers which can be preferably used are polyvinyl methyl ether products, such as a 30% aqueous solution (manufactured by Tokyo Chemical Industry Co., Ltd.) and Lutonal M (trademark, manufactured by BASF); methylcellulose products such as Metolose SM-15 (Shin-Etsu Chemical Co., Ltd.), Marpolose (Matsumoto Yushi Seiyaku Co., Ltd.); and the like.

Among the above-mentioned thermosensitive polymers, cellulose derivatives such as methylcellulose, hydroxypropylcellulose, hydroxypropylmethylcellulose, and the like are particularly effective, because they exhibit a relatively small mutual interaction between themselves and various volatile effective components (e.g., perfumes), surfactants, and the like. Although the reason for this small mutual interaction has not been completely determined, it is presumed that these thermosensitive polymers possess a chain structure of which the free rotation is restricted, and this structure contributes to the restriction of the mutual interaction between the thermosensitive polymers and the volatile effective components (such as perfumes), surfactants, and the like.

The temperature at which the volatilization suppressing agent exhibits its effects, i.e., the temperature at which the thermosensitive polymer aggregates or gels, is normally between 10° C. and 90° C., although this temperature varies depending on the type of the polymer, the concentration of the polymer, coexisting substances, and the like.

It is desirable to experimentally determine the aggregating or gelling temperature of the volatilization suppressing agent, which differs depending on the type and the structure of the thermosensitive polymer. The experiment can be carried out, for example, by heating the volatilization suppressing agent and determining the temperature at which the aggregation or gelation begins.

The aggregating or gelling temperature thus determined, is, for example, in the case of methylcellulose, about 62° C.; hydroxypropylmethyl-cellulose, about 65° C.; polyvinyl methyl ether, about 32° C.; and partially acetylated polyvinyl alcohol, about 32° C. (degree of acetylation: 30%) or about 58° C. (degree of acetylation: 20%).

It is possible, therefore, to select a thermosensitive polymer having a aggregating or gelling temperature most suited to the purpose of use of the individual volatilization suppressing agent.

In addition, it is possible to use either a volatilization suppressing agent containing one kind of thermosensitive polymer or an agent containing two or more kinds of thermosensitive polymers.

Furthermore, the aggregating or gelling temperature may be adjusted by the addition of a solvent (e.g., alcohol) or an inorganic salt (e.g., magnesium sulfate).

The volatilization suppressing agent of the present invention may be prepared in the form of a solution by dissolving the thermosensitive polymer, which is the effective component, in an aqueous solvent such as water, or in the form of a powder comprising the thermosensitive polymer, which can be added directly to the aqueous composition of the volatile component.

The volatilization suppressing agent of the present invention thus prepared can be added to volatile compositions.

The amount of the volatilization suppressing agent to be added to a volatile composition is normally about 0.1–30%, although this amount varies depending on the type of volatile component, the type of thermosensitive polymer, the manner in which the composition is used, as discussed later in this specification, and the like.

In the present invention, the term "volatile composition" means a composition comprising water as a main medium, and may be in the form of a solution, a solubilized composition, an emulsion, an aqueous gel, or the like, with said volatile component incorporated therein in any optional form. Such volatile compositions include air fresheners or aromatic compositions, deodorants, insecticides, moth proofers, repellents, attractants, antimicrobial or antifungal agents, antioxidants, ozone decomposition agents, and the like.

Specifically, the solubilized composition is prepared by using a nonionic surfactant, such as, for example, polyoxyethylene alkyl ether, polyoxyethylene alkylphenyl ether, polyoxyethylene styrylphenyl ether, polyoxyethylene-polyoxypropylene glycol, polyhydric alcohol fatty acid partial ester, polyoxyethylene fatty acid ester, polyoxyethylene adduct of castor oil, or polyoxyethylene alkylamine; an anionic surfactant, such as, for example, a salt of fatty acid, alkylbenzene sulfonate, alkyl sulfonate, dialkyl sulfosuccinate, alkyl sulfate, polyoxyethylene alkyl ether sulfate, or alkyl phosphate; or the like.

For the preparation of the emulsion, casein, lecithin, gum arabic, cationic surfactants, glycols, lanolin, and the like may be used in addition to said surfactants.

A gelling agent, such as, for example, agar, proteoglycan, glycoprotein, pectic acid, pectinic acid, arginic acid, carrageenan, gellan gum, guar gum, xanthane gum, locust bean gum, pectin, gelatin, casein, starch, galactomannan, carboxymethylcellulose, polyacrylic acid and its salts, or the like, is used for the preparation of the aqueous gel.

Examples of specific embodiments of the form in which the volatilization suppressing agent of the present invention is used are as follows.

A first embodiment is an addition of a thermosensitive polymer to water or an aqueous composition of a volatile component, which volatilizes directly into the air.

The mechanism of volatilization suppression by the addition of the volatilization suppressing agent to an aqueous medium in this type of embodiment has not been fully determined. A possible mechanism may be that the aggregation or gelation of the thermosensitive polymer contained in the volatilization suppressing agent, which takes place as the temperature rises, induces formation of a film-like or membrane-like matter on the surface of the aqueous composition, or increases the viscosity of the entire aqueous composition, thus making it difficult for the volatile component therein to move to the surface of the composition.

Especially preferred thermosensitive polymers for use in this type of embodiment are polymers which thermoreversibly gel when the temperature of the aqueous solution containing the polymers increases. A specific example of this type of polymer is methylcellulose. The mechanism of the volatilization suppression in the composition using this type of polymer is considered to be related to the increase in the viscosity caused by the gelation of the thermosensitive polymer.

Included in preferred applications of this type of embodiment are a system for controlling humidity by the addition of the volatilization suppressing agent to water, an aqueous gel type air freshener, and the like.

Another embodiment is an addition of a thermosensitive polymer to an aqueous composition of a volatile component, which is designed to volatilize through pores or capillaries.

The volatilization suppressing mechanism in this type of embodiment is considered to be related to the fact that the thermosensitive polymer aggregates or gels as the temperature goes up and adheres to pores or capillaries to preclude the movement and volatilization of the liquid containing a volatile component.

Liquid air fresheners, liquid moth proofers, liquid repellents, liquid insecticides, ceramic air fresheners, and blotter air fresheners are given as examples of preferred applications of this type of embodiment.

Pores or capillaries used in this type of embodiment include those present in media such as paper, fiber, nonwoven fabric, fused resins, ceramics, sintered metals, and the like.

An especially preferred example of this type of embodiment is prepared by adding the volatilization suppressing agent to a liquid aromatic composition which is used in a liquid air freshener with a wick inserted in a container. One example of such a system will now be described with reference to FIG. 1.

FIG. 1 is a longitudinal cross-sectional view of a liquid air freshener system which comprises a container 1, a wick 2 inserted therein and a volatilizing plate 3. The liquid aromatic composition 4 comprising the volatilization suppressing agent of the present invention is freely moving liquid at normal use temperatures so that it is smoothly supplied to the volatilizing plate 3 via the wick 2.

If the temperature rises, however, the volatilization suppressing agent in the aromatic composition 4 aggregates or gels, and the resulting aggregate or gel prevents the liquid from moving freely through the wick 2. This reduces the amount of the aromatic composition supplied to the volatilizing plate 3, thus suppressing the volatilization rate of the volatile component. When the temperature goes down, the volatilization suppressing agent regains its water-solubility and is no longer the aggregated or gelled state, so that it no more interferes with the liquid transfer through the wick. Thus, the composition volatilizes the same amount of the volatile component as it did before the temperature rise.

Although the liquid air freshener system of the volatilization controlling type shown in FIG. 1 has a volatilization plate 3, it is not necessarily limited to the construction. The volatile component may be volatilized directly from the wick.

It is possible to confirm that the aqueous composition to which the volatilization suppressing agent of the present invention has been added is exhibiting the desired effects by observation with the naked eye, because the composition becomes turbid when the volatilization suppressing agent begins to exhibit its effect. This characteristic can be used to indicate that the temperature rises beyond a certain level, if the aqueous composition is filled into a transparent container.

Furthermore, in the case of an aqueous gel composition using carrageenan, for example, as the gelling agent, generally the gel becomes soft as the temperature rises. If methylcellulose is added as the volatilization suppressing agent, the methylcellulose gels as the temperature rises and prevents the gel from becoming soft. As a result, methylcellulose can act to raise the softening point of the aqueous gel composition.

The combined use of a gelling agent and the volatilization suppressing agent of the present invention, therefore, makes it possible to maintain the gel state of the composition over a wide temperature range.

As illustrated above, the use of the volatilization suppressing agent of the present invention can suppress volatilization of volatile components when the temperature rises and, as a result, volatilization of the volatile components is less affected by the temperature change.

It is therefore possible to volatilize volatile components more economically and to prevent problems due to excessive volatilization.

Other features of the invention will become apparent in the following description of the exemplary embodiment which is given for illustration of the invention and is not intended to be limiting thereof.

EXAMPLE

Example 1

<Measurement of turbidity change and the rate of volatilization of an aqueous solution to which polyvinyl methyl ether has been added>

A solution containing 1% of polyvinyl methyl ether (reagent grade, supplied by Tokyo Chemical Industry Co., Ltd.) as a thermosensitive polymer (such a solution is herein referred to as Invention Aqueous Solution 1) was prepared and its thermal change was determined by measuring the turbidity change. The turbidity was evaluated by observation with the naked eye, in which samples were compared with a completely transparent solution (turbidity=0) and five standard solutions with different turbidities (turbidity=1–5), with the turbidity of the completely opaque solution being 5.

Figure 2:
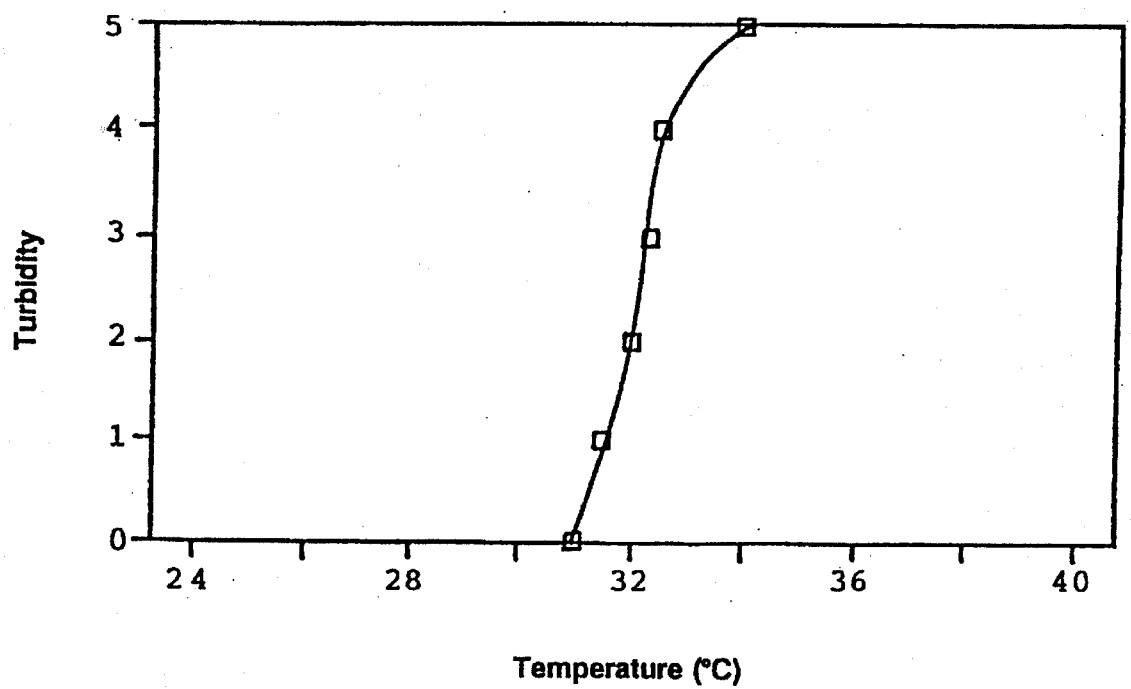
FIG. 2 is a graph showing the relationship between the temperature and the turbidity of an aqueous solution to which the volatilization suppressing agent of the present invention has been added.

The results are shown in FIG. 2, based on which the aggregation temperature of Invention Aqueous Solution 1 was determined to be about 32° C.

100 g of Invention Aqueous Solution 1 was charged into a 100 ml beaker to measure the rate of volatilization at 25° C. and 60° C. For comparison, the rate of volatilization of water containing no thermosensitive polymer (Comparative Solution 1) was measured in the same manner.

As a result, the rates of volatilization of Invention Aqueous Solution 1 at 25° C. and 60° C. were found to be 0.3 g/hr and 1.3 g/hr, and those of Comparative Solution 1, 0.4 g/hr and 2.0 g/hr, respectively.

The rate of volatilization was measured from the volatilized amount (g) per hour.

Example 2

<Measurement of the rate of volatilization from a liquid-wick type volatilization container of aqueous solution to which polyvinyl methyl ether has been added>

180 g of Invention Aqueous Solution 1 prepared in Example 1 was charged into the same liquid-wick type volatilization container as shown in FIG. 1 to measure the rates of volatilization at 25° C., 30° C., 40° C., and 50° C. in the same manner as in Example 1. For comparison, the rate of volatilization of Comparative Solution 1 (water containing no thermosensitive polymer) was measured in the same manner.

The results are shown in Table 1.

TABLE 1

| | Rate of volatilization (g/hr) | |
|---|---|---|
| Temperature | Invention Aqueous Solution 1 | Comparative Solution 1 |
| 25° C. | 1.0 | 1.2 |
| 30° C. | 1.1 | 1.1 |

TABLE 1-continued

| | Rate of volatilization (g/hr) | |
|---|---|---|
| Temperature | Invention Aqueous Solution 1 | Comparative Solution 1 |
| 40° C. | 1.5 | 1.6 |
| 50° C. | 0.5 | 2.4 |

Example 3

<Measurement of the rate of volatilization of a volatile moth proofer composition to which polyvinyl methyl ether has been added>

A volatile moth proofer composition containing 2% of methyl carbamate and 1% of polyvinyl methyl ether (the same reagent grade product as used in Example 1) was prepared. The solution is herein referred to as Invention Aqueous Solution 2. The aggregation temperature of this solution was about 32° C.

100 g of Invention Aqueous Solution 2 was charged into the same liquid-wick type volatilization container as used in Example 2. The rates of volatilization at 25° C. and 50° C. were measured in the same manner as in Example 1 and found to be 0.8 g/hr at both temperatures. For comparison, the rates of volatilization of a 2% methyl carbamate aqueous solution which contained no thermosensitive polymer (Comparative Solution 2) were measured under the same conditions and found to be 0.8 g/hr (25° C.) and 1.8 g/hr (50° C.).

Figure 3:
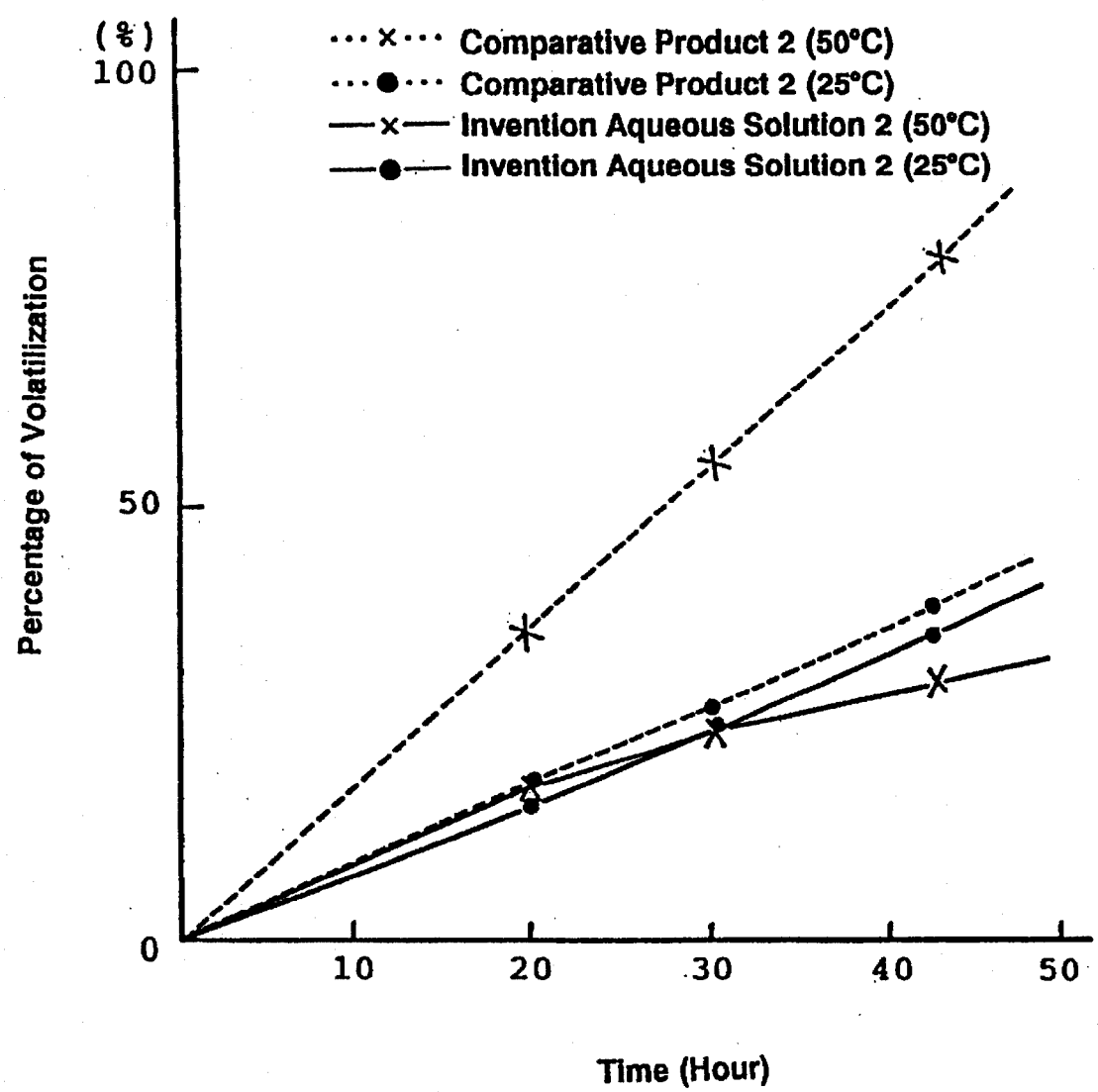
FIG. 3 is a graph showing the relationship between the volatilization temperature and the percentage of volatilization of an aqueous moth proofer solution from a liquid-wick container to which the volatilization suppressing agent of the present invention has been added.

In addition, the percentage of volatilization, which is the percentage of the volatilized amount (weight) to the total original amount (weight), up to 50 hours was measured. The results are shown in FIG. 3.

Example 4

<Measurement of the rate of volatilization of an aromatic composition to which polyvinyl methyl ether has been added>

An aqueous aromatic composition containing 1% of polyvinyl methyl ether was prepared by dissolving polyvinyl methyl ether into rose water (Invention Aqueous Solution 3). The aggregation temperature of this solution was about 35° C.

100 g of Invention Aqueous Solution 3 was charged into the same liquid-wick type volatilization container as used in Example 2. The rate of volatilization at 50° C. was measured in the same manner as in Example 1 and found to be 0.6 g/hr. For comparison, the rate of volatilization of rose water containing no thermosensitive polymer (Comparative Solution 3) was measured under the same conditions and found to be 2.0 g/hr.

Example 5

<Measurement of the rate of volatilization of an aqueous fungicidal composition to which polyvinyl methyl ether has been added>

An aqueous fungicidal composition containing 2% of Biocide 800S (trademark: a product of Taisho Co.) and 1% of polyvinyl methyl ether was prepared (Invention Aqueous Solution 4). The aggregation temperature of this solution was about 32° C.

100 g of Invention Aqueous Solution 4 was charged into the same liquid-wick type volatilization container as used in Example 2. The rate of volatilization at 50° C. was measured in the same manner as in Example 1 and found to be 1.5 g/hr. For comparison, the rate of volatilization of 2% Biocide 800S aqueous solution containing no thermosensitive polymer (Comparative Solution 4) was measured under the same conditions and found to be 2.1 g/hr.

Example 6

<Measurement of the rate of volatilization of an aqueous solution to which methylcellulose has been added>

An aqueous solution containing 1% of methylcellulose (Metlose SM-15: trademark, a product of Shin-Etsu Chemical Co., Ltd.) as a thermosensitive polymer was prepared (Invention Aqueous Solution 5). The gelling temperature of this solution was about 60° C.

100 g of Invention Aqueous Solution 5 was charged into a 100 ml beaker to measure the rate of volatilization at 25° C. and 60° C. The rates of volatilization at 25° C. and 60° C. were found to be 0.3 g/hr and 0.9 g/hr, respectively. For comparison, the rates of volatilization of an aqueous solution containing no thermosensitive polymer (Comparative Solution 5) were measured under the same conditions and found to be 0.4 g/hr (25° C.) and 2.2 g/hr (60° C.).

Example 7

<Measurement of the turbidity changes in aromatic solutions to which methylcellulose and a solubilizing agent have been added>

Aromatic compositions were prepared from various perfumes shown in Table 2 and 2.0 g of a solubilizing agent by placing them in 100 ml beakers and slowly charging water to make the total volume 50 ml, while stirring by a magnetic stirrer.

Invention Solubilized Compositions 6 were prepared by adding 50 g of 2.0% aqueous solution of methylcellulose used in Example 6 to each aromatic composition.

As the solubilizing agent, a mixture of 30% of surfactant HPS-N598A (trademark, manufactured by Nippon Shokubai Kagaku Kogyo Co., Ltd.), 50% of polyoxyethylenenonylphenol (EO 10 mol), and 20% of sodium dialkylsulfosuccinate was used.

The turbidity changes and gelling temperature of Invention Solubilized Compositions 6 were measured in the same manner as in Example 1. The results are shown in Table 2.

TABLE 2

| | Amount (g) | Gelling temperature (°C.) |
|---|---|---|
| α-Pinene | 0.5 | 60 |
| Cinnamic aldehyde | 0.5 | 57 |
| 6-Methyl-5-hepten-2-one | 1.0 | 60 |
| Isoamyl acetate | 1.0 | 60 |
| Phenylpropyl alcohol | 1.0 | 53 |

Example 8

<Measurement of the rate of volatilization from a liquid-wick type container of an aromatic composition to which methylcellulose and a solubilizing agent have been added>

2.0 g of a citrus perfume was charged into to a 100 ml beaker together with 4.0 g of the solubilizing agent used in Example 7. Water was then added slowly to make the total amount 50 g, while stirring by a magnetic stirrer at room temperature, thus obtaining an aromatic composition.

Invention Solubilized Composition 7 was prepared by adding 50 g of 2.0% aqueous solution of methylcellulose used in Example 6 to said aromatic composition. The gelling temperature of Invention Solubilized Composition 7 was about 60° C.

50 g of Invention Solubilized Composition 7 was charged into the liquid-wick type volatilization container shown in FIG. 1. The rates of volatilization at 25° C. and 60° C. were measured in the same manner as in Example 1 and found to be 0.5 g/hr and 0.6 g/hr, respectively. For comparison, the rates of volatilization of an aromatic composition containing 2.0% of the citrus perfume and 4.0% of the solubilizing agent, but containing no thermosensitive polymer (Comparative Composition 6) were measured under the same conditions. The rates of volatilization were found to be 0.5 g/hr (25° C.) and 2.2 g/hr (60° C.).

Example 9

<Measurement of the rate of volatilization from a paper volatilizer of an aromatic composition to which methylcellulose and a solubilizing agent have been added>

Laminated filter paper (diameter: 95 mm, thickness: about 10 mm) was impregnated with 40 g of Invention Solubilized Composition 7 prepared in Example 8. The impregnated filter paper was placed on a Petri's dish and the rate of volatilization was measured at 25° C. and 60° C. in the same manner as in Example 1. The rates of volatilization were found to be 1.2 g/hr (25° C.) and 2.5 g/hr (60° C.). For comparison, the rates of volatilization of Comparative Composition 6 were measured under the same conditions and found to be 1.3 g/hr (25° C.) and 3.1 g/hr (60° C.).

Example 10

<Measurement of the rate of volatilization of an aqueous gel aromatic composition to which methylcellulose and a solubilizing agent have been added>

6.0 g of a citrus perfume was charged into to a 300 ml beaker together with 12.0 g of the solubilizing agent used in Example 7. The mixture was stirred by a magnetic stirrer at room temperature.

7.0 of carrageenan was placed in another 300 ml beaker and water was added to it to make the total amount 200 g. The mixture was heated at about 80° C. while stirring by a magnetic stirrer to dissolve carrageenan in water. This solution was added to said beaker containing the mixture of the perfume and the solubilizing agent to make the total amount 200 g. The mixture was stirred by an electric stirrer while maintaining the temperature at about 60° C., thus obtaining an aqueous gel aromatic composition. 100 g of 5% aqueous solution of methylcellulose used in Example 6 was added to this aqueous gel aromatic composition while maintaining the temperature at about 60° C., thus obtaining Invention Aqueous Gel 8.

100 g of Invention Aqueous Gel 8 was charged into a 100 ml beaker to measure the rate of volatilization at 25° C. and 60° C. in the same manner as in Example 1. The rates of volatilization were found to be 0.3 g/hr and 0.9 g/hr, respectively. For comparison, the rate of volatilization of an aqueous aromatic composition containing 2.0% of the citrus perfume and 4.0% of the solubilizing agent, and about 2.3% of carrageenan, but containing no thermosensitive polymer (Comparative Aqueous Gel 7) were measured under the same conditions. The rates of volatilization were found to be 0.3 g/hr (25° C.) and 1.1 g/hr (60° C.).

Example 11

<Measurement of the rate of volatilization of an aqueous gel aromatic composition to which methylcellulose and a solubilizing agent have been added>

2.0 g of a citrus perfume was placed in a 100 ml beaker together with 6.0 g of the solubilizing agent, which is a mixture of 40% of surfactant HPS-N598A and 60% of polyoxyethylenenonylphenol (EO 10 mol). The mixture was stirred by a magnetic stirrer at room temperature.

1.5 g of gellan gum placed in another 100 ml beaker and water was added to it to make the total amount 100 g. The mixture was heated at about 90° C. while stirring by a magnetic stirrer to dissolve gellan gum in water. 2 g of 2% aqueous solution of calcium chloride was further added and the solution was stirred. This gellan gum solution was added to said beaker containing the mixture of the perfume and the solubilizing agent to make the total volume 50 g. The mixture was stirred by a magnetic stirrer while maintaining the temperature at about 50° C., thus obtaining an aqueous gel aromatic composition. 50 g of 2% aqueous solution of methylcellulose used in Example 6 was added to this aqueous gel aromatic composition while maintaining the temperature at about 50° C., thus obtaining Invention Aqueous Gel 9.

100 g of Invention Aqueous Gel 9 was charged into a 100 ml beaker to measure the rate of volatilization at 25° C. and 60° C. in the same manner as in Example 1. The rates of volatilization were found to be 0.5 g/hr and 1.2 g/hr, respectively. For comparison, the rate of volatilization of an aqueous gel aromatic composition containing 2.0% of the citrus perfume, 6.0% of the solubilizing agent, and about 0.75% of gellan gum, but containing no thermosensitive polymer (Comparative Aqueous Gel 8) was measured under the same conditions. The rates of volatilization were found to be 0.5 g/hr (25° C.) and 1.4 g/hr (60° C.).

Obviously, numerous modifications and variations of the present invention are possible in light of the above teachings. It is therefore to be understood that within the scope of the appended claims, the invention may be practiced other than as specifically described herein.

What is claimed is:

1. An air freshener system, comprising a container, said container containing a volatile liquid composition and a wick which penetrates said volatile composition, said volatile liquid composition comprising a volatile effective component, and an effective amount of a volatilization suppression agent, the effective amount being sufficient to decrease the rate of volatilization of said volatile liquid as the temperature increases, said volatile suppression agent comprising at least one thermosensitive polymer and the volatile liquid composition having a characteristic of thermoreversibly aggregating or gelling as its temperature increases.

2. The air freshener system according to claim 1, wherein said thermosensitive polymer is selected from the group consisting of methylcellulose, hydroxypropylcellulose, hydroxypropylmethylcellulose, partially acetylated polyvinyl alcohol, polyvinyl methyl ether, polyethylene oxide, and poly-N-isopropylacrylamide.

3. The air freshener system according to claim 1, wherein said thermosensitive polymer is about 0.1–30% by weight of said volatile liquid composition.

4. The air freshener system according to claim 3, wherein said thermosensitive polymer is selected from the group consisting of methylcellulose, hydroxypropylcellulose, hydroxypropylmethylcellulose, partially acetylated polyvinyl alcohol, polyvinyl methyl ether, polyethylene oxide, and poly-N-isopropylacrylamide.

5. The air freshner system according to claim 1, wherein said thermosensitive polymer is a partially acetylated polyvinyl alcohol.

6. The air freshner system according to claim 5, wherein the degree of acetylation of said polyvinyl alcohol is between 20–30%.

7. The air freshener system according to claim 1 further including a volatilization plate in physical contact with said wick.

8. An air freshener system comprising, a container said container containing a volatile liquid composition, a wick which penetrates said volatile composition, said volatile composition comprising an effective component carried by a volatile solvent and an effective amount of a volatilization suppression agent, the effective amount being sufficient to decrease the rate of volatilization of said volatile liquid as the temperature increases, said volatilization suppression agent comprising at least one thermosensitive polymer and the volatile liquid having a characteristic of thermoreversibly aggregating or gelling as its temperature increases.

9. The air freshener system according to claim 8, wherein said thermosensitive polymer is selected from the group consisting of methylcellulose, hydroxypropylcellulose, hydroxypropylmethylcellulose, polyvinyl methyl ether, partially acetylated polyvinyl alcohol, polyethylene oxide, and poly-N-isopropylacrylamide.

10. The air freshener system according to claim 9, wherein said thermosensitive polymer is partially acetylated polyvinyl alcohol and the degree of acetylation of said polyvinyl alcohol is between 20–30%.

11. The air freshener system according to claim 8, wherein said thermosensitive polymer is about 0.1–30% by weight of said volatile liquid composition.

12. The air freshener system according to claim 8, further including a volatilization plate on top of said wick.

* * * * *

UNITED STATES PATENT AND TRADEMARK OFFICE
CERTIFICATE OF CORRECTION

PATENT NO. : 5,534,229
DATED : July 9, 1996
INVENTOR(S) : Nomura Ryuji et al.

It is certified that error appears in the above-indentified patent and that said Letters Patent is hereby corrected as shown below:

On the title page, item
   (73) Assignee:

"Nomura & Shibatani, Tokyo, Japan" should read
      --S.T. Chemical Co., Ltd., Tokyo, Japan--.

Signed and Sealed this

Fourth Day of March, 1997

*Attest:*

BRUCE LEHMAN

*Attesting Officer*      *Commissioner of Patents and Trademarks*